United States Patent [19]

Kocur et al.

[11] Patent Number: 5,258,358
[45] Date of Patent: Nov. 2, 1993

[54] LIQUID HERBICIDAL COMPOSITIONS CONTAINING GLUFOSINATE AND AN ALKYL POLYGLYCOSIDE

[75] Inventors: Jean Kocur, Hofheim am Taunus; Thomas Maier, Frankfurt am Main; Peter Langelüddeke, Hofheim am Taunus; Martin Hess, Mainz, all of Fed. Rep. of Germany

[73] Assignee: Hoechst Aktiengesellschaft, Frankfurt am Main, Fed. Rep. of Germany

[21] Appl. No.: 873,417

[22] Filed: Apr. 24, 1992

[30] Foreign Application Priority Data

Apr. 27, 1991 [DE] Fed. Rep. of Germany ....... 4113867

[51] Int. Cl.$^5$ ............................................. H01N 57/04
[52] U.S. Cl. .................................... 504/205; 504/116; 504/127; 71/DIG. 1
[58] Field of Search ............. 71/86, DIG. 1; 504/205, 504/116, 127

[56] References Cited

U.S. PATENT DOCUMENTS

| H224 | 3/1987 | Malik et al. | 71/92 |
|------|--------|--------------|-------|
| 4,168,963 | 9/1979 | Rupp et al. | 71/86 |
| 4,400,196 | 8/1983 | Albrecht et al. | 71/86 |

FOREIGN PATENT DOCUMENTS

| 0048436 | 3/1982 | European Pat. Off. . |
| 0317260 | 5/1989 | European Pat. Off. . |
| 3809159 | 9/1989 | Fed. Rep. of Germany . |

*Primary Examiner*—Allen J. Robinson
*Assistant Examiner*—B. Bembenick
*Attorney, Agent, or Firm*—Curtis, Morris & Safford

[57] ABSTRACT

The invention relates to liquid herbicidal compositions comprising a compound of the formula

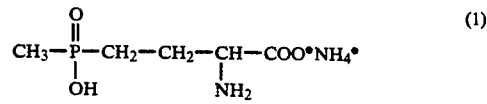 (1)

and an alkyl polyglycoside or an alkyl polyglycoside and at least one surfactant from the series comprising fatty alcohol polyglycol ether sulfate, alkyldimethylamine oxide, alkyldimethylbenzylammonium chloride and coconut alkyldimethylaminoacetic acid or a salt thereof. The invention furthermore relates to a process for the preparation of these compositions and their use for controlling undesired vegetation.

11 Claims, No Drawings

LIQUID HERBICIDAL COMPOSITIONS CONTAINING GLUFOSINATE AND AN ALKYL POLYGLYCOSIDE

DESCRIPTION

The invention relates to novel formulations of glufosinate-ammonium, the ammonium salt of 4-[hydroxy(methyl)-phosphinoyl]-D,L-homoalanine (I)

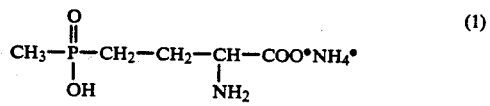

It is known from U.S. Pat. No. 4,168,963 and from Z. Pfl. Krankh. Pfl. Schutz, Special Edition IX, 431-440, 1981, that the compound of the formula I has a good and broad activity against weeds of a large number of botanical families.

Formula I embraces all stereoisomers (D- and L-form), preferably the biologically active L-enantiomer, and stereoisomer mixtures including the racemate.

It is known from EP-A-0,048,436 that coconut fatty alkyl benzyldimethylammonium chloride or ($C_{12}$–$C_{18}$)-alkyl polyglycol ether sulfates enhance the action of I. However, the aqueous liquid formulations of I are only stable when polar solvents such as dimethylformamide, N-methylpyrrolidone or ethylene glycol monomethyl ether are added to them. If not, the phases in the formulations separate into phases which are enriched with active substance and low in surfactant and phases which are low in active substance and enriched with surfactant. The use of the abovementioned solvents is particularly necessary in the case of formulations which are high in ($C_{12}$–$C_{18}$)-fatty alcohol polyglyol ether sulfates.

Due to the increasingly critical attitude towards solvents, in particular from toxicological points of view, the use of substantial concentrations of these substances can have disadvantages.

Formulations of the active substance I should therefore be free from solvents or contain only small amounts of solvents.

It has furthermore emerged that the stability of these formulations, which are disclosed in this EP-A, to low temperatures is frequently insufficient for practical requirements, in particular when surfactant contents are high.

Even though active substance and wetting agent only precipitate at temperatures below 0° C., there are still handling difficulties when large containers which had been stored under frost conditions are dispensed into small containers since these containers must first be stored under warm conditions for a prolonged period and the product must then be homogenized.

Formulations of the active substance I should therefore remain homogeneous and free-flowing even when temperatures are below 0° C.

Surprisingly, it has now been found that formulations with a very low solvent content and even solvent-free formulations of the active substance I which are highly stable to low temperatures and have a good biological action can be prepared by using certain surfactants or surfactant mixtures.

The invention therefore relates to a liquid herbicidal composition which comprises a compound of the formula I in the form of the stereoisomer mixture or of the L-enantiomer and a surfactant from the series of the ($C_8$–$C_{14}$)alkyl polyglycosides, if appropriate as a mixture with ($C_{10}$–$C_{18}$)-fatty alcohol polyglycol ether sulfates,
($C_{12}$–$C_{18}$)alkyldimethylamine oxides,
($C_{10}$–$C_{18}$)alkyldimethylbenzylammonium chloride and/or coconut alkyldimethylaminoacetic acid (betaine), where, in the case of the ether sulfates, the alkali metal salts, ammonium salts or alkaline earth metal salts can be used.

In the form of an aqueous dilution, the compositions according to the invention comprise 0.5 to 40 % by weight, preferably 1 to 30 % by weight, of the active substance of the formula I and 0.5 to 8 parts of the surfactants according to the invention per part of active substance and 0 to 10 % by weight of a solvent which is miscible with water and acceptable for use in crop protection, such as methyl glycol, propylene glycol monomethyl ether, PEG 200, isopropanol, DMF or NMP.

In the case of a mixture of alkyl polyglycoside with at least one surfactant from the series comprising ($C_{10}$–$C_{18}$)fatty alcohol polyglycol ether sulfate, ($C_{12}$–$C_{18}$)alkyldimethylamine oxide, ($C_{10}$–$C_{18}$)alkyldimethylbenzylammonium chloride and coconut alkyldimethylaminoacetic acid, the amount of alkylpolyglycoside is preferably not more than 50 % by weight of the entire surfactant content.

Up to 25 % by weight, preferably up to 15 % by weight, of further commercially available adjuvants, for example surfactants, such as wetting agents, dispersants and adhesion promoters, defoamers, preservatives and antifreeze agents, can be added to the compositions according to the invention.

Suitable additional wetting and dispersing agents are, for example, tributylphenol polyglycol ethers, such as the ®Sapogenat T brands (Hoechst), nonylphenol polyglycol ethers, such as the ®Arkopal N brands (Hoechst) or isotridecanol polyglycol ethers, such as the Genapol X brands (Hoechst).

Examples of suitable defoamers are those from the group the perfluoro-($C_6$–$C_{18}$)alkylphosphinic acids or -phosphonic acids (see DE-A-4,021,336).

If necessary, preservatives can be used, for example those based on formaldehyde, benzoic acid or triphenylotin, such as, for example, ®Kobate C.

It is also possible to add antifreeze agents such as urea, salts (for example ammonium sulfate), polyols (for example glycol, propylene glycol or glycerol) or sugars.

The surfactants mentioned can also be employed advantageously in combined formulations of I with other herbicidal active substances such as, for example, atrazine, linuron, monolinuron, isoproturon, thidiazuron, simazine, diuron, metolachtor, oxyfluorfen, bifenox, imazethapyr, imazethabenz, imazaquin, quizalofop-P-tefuryl (UBI-C 4874), sulfonylureas, such as DPX-L-5300, thiameturon-methyl, metsulfuron-methyl or nicosulfuron (Ishihara), where they can enhance the action of I.

It is also possible to add the surfactants directly to the spray liquor of the active substance solution of I or the mixed formulations with the herbicides mentioned, before application. The invention also relates to the dilute preparations (spray liquors) which contain the components of the concentrated preparations according to the invention in the form of an up to 500-fold dilution.

The compositions according to the invention exist in the form of solutions, and in mixtures with water-insoluble active substances such as, for example, the above-mentioned herbicidally active triazine and urea compounds, in the form of suspension concentrates, which contain the insoluble active substances in the solid phase, and the compound I and the surfactants according to the invention in the aqueous liquid phase. Active substances which have a low melting point or liquid active substances such as metolachtor, alachlor, trifluralin, esters of the phenoxy herbicides or esters of ioxynil or bromoxynil are prepared with a compound I and the surfactants in the form of a stable emulsion which contains the compound I and the surfactants according to the invention in the aqueous phase and the water-insoluble liquid active substance, or the active substance which is dissolved in organic solvents, in the "oily" liquid phase, where the organic solvents themselves should not be water-soluble.

Such mixed formulations can be prepared in a variety of ways. On the one hand, a procedure can be followed in which the individual components are prepared separately in the form of single dispersions and solutions, and these are then mixed using a colloid mill. On the other hand, it is possible to grind the active substances of the finely dispersed phase together and to add the active substance solution to this mixed dispersion. In principle, it is also possible to process all active substances in one pass to give the desired mixed formulation.

The combined formulations prepared in this manner are storage-stable, undergo virtually no chemical changes and are simple to handle on use.

In general, the compositions according to the invention are applied after dilution with water, but they can also be applied in undiluted form.

To prepare the compositions according to the invention, the active substance is dissolved in water, the calculated amount of potentiating surfactant and, if appropriate, further customary adjuvants such as solubilizers (propylene glycol monomethyl ether, glycols, polyglycols, block copolymers, DMF, N-methylpyrrolidone, and others), and other wetting agents, colorants or defoamers (for example silicones, polyethylene polypropylene glycols, soaps etc.) are added, and the batch is mixed intimately. Small amounts of solids are removed by filtration.

The following may be mentioned as examples of the surfactants according to the invention:

Fatty alcohol $C_8$–$C_{10}$ glucoside: ®Plantaren APG 225 (Henkel KG)

Fatty alcohol polyglycol ether sulfates: ®Genapol LRO, Genapol ARO, Genapol ZRO (Hoechst AG) ®Texapon ASV, Texapon Na, Texapon M (Henkel KG)

($_{12}$–$C_{18}$)alkyldimethylamine oxides: ®Alkamox LO (Alkaril Chemicals) ®Genaminox (Hoechst AG)

($C_{10}$–$C_{18}$)alkyldimethylbenzylammonium chloride: ®Dodigen brands (Hoechst AG)

Coconut alkyldimethylaminoacetic acid: ®Alkazeric CB (Alkaril Chemicals).

The examples of Table 1 which follow are intended to illustrate the invention without imposing a restriction thereto (percentages are by weight).

| | Abbreviations: |
|---|---|
| prop. m. | propylene glycol monomethyl ether |
| det. | detergent |
| org. s. | organic solvent |
| m. glyc. | methyl glycol |

TABLE 1

| Formulation No. | Active subst. % | Water % | org. s. % | | Surfactant % det. | Appearance at 20° C. | 0° C. | below 0° C. |
|---|---|---|---|---|---|---|---|---|
| Comparison composition 1 | 19 D,L | 41 | 20 m. glyc. | 20 | Na fatty alcohol polyglycol ether sulfate | clear | clear | cloudy, highly-viscous, pasty |
| Comparison composition 2 | 13.5 D,L | 36.5 | 10 prop. m | 40 | Na fatty alcohol polyglycol ether sulfate | clear | cloudy | cloudy, highly-viscous, pasty |
| 2 | 18 D,L | 61 | — | 21 | fatty alcohol $C_8$–$C_{10}$-glycoside | clear | clear | fluid to −16° C., clear |
| 3 | 18 D,L | 51 | 10 prop. m | 21 | fatty alcohol $C_8$–$C_{10}$-glycoside | clear | clear | fluid to −25° C., clear |
| 4 | 18 D,L | 56 | — | 26 | fatty alcohol $C_8$–$C_{10}$-glycoside | clear | clear | fluid to −15° C., clear |
| 5 | 18 D,L | 46 | 10 prop. m | 26 | fatty alcohol $C_8$–$C_{10}$-glycoside | clear | clear | fluid to −25° C., clear |
| 6 | 13 D,L | 46 | — | 41 | fatty alcohol $C_8$–$C_{10}$-glycoside | clear | clear | fluid to −17° C., clear |
| 7 | 13 D,L | 36 | 10 prop. m | 41 | fatty alcohol $C_8$–$C_{10}$-glycoside | clear | clear | fluid to −20° C., clear |
| 8 | 18 D,L | 51 | 10 prop. m | 10.5 10.5 | fatty alcohol $C_8$–$C_{10}$-glycoside Na fatty alcohol polyglycol ether sulfate | clear | clear | fluid to −13° C., clear |
| 9 | 18 D,L | 61 | — | 10.5 10.5 | fatty alcohol $C_8$–$C_{10}$-glycoside Na fatty alcohol polyglycol ether sulfate | clear, slightly viscous | clear, viscous | clear to −9° C., viscous but still flowable |
| 10 | 18 D,L | 61 | — | 14 7 | fatty alcohol $C_8$–$C_{10}$-glycoside Na fatty alcohol polyglycol ether sulfate | clear | clear | clear to −15° C., fluid |
| 11 | 18 D,L | 61 | — | 10.5 10.5 | fatty alcohol $C_8$–$C_{10}$-glycoside coconut alkyldimethylamine oxide | clear, slightly viscous | clear, viscous | clear to −8° C., viscous but still flowable |
| 12 | 18 D,L | 61 | — | 10.5 | fatty alcohol | clear | clear | clear to −12° C., |

TABLE 1-continued

| Formulation No. | Active subst. % | Water % | org. s. % | | Surfactant % det. | Appearance at | | |
|---|---|---|---|---|---|---|---|---|
| | | | | | | 20° C. | 0° C. | below 0° C. |
| 13 | 18 D,L | 56 | 5 prop. m | 10.5 | C$_8$-C$_{10}$-glycoside | | | fluid |
| | | | | 10.5 | coconut alkyldimethylbenzylammonium chloride | clear | clear | clear to −8° C., fluid |
| | | | | | fatty alcohol | | | |
| 14 | 18 D,L | 56 | 5 prop. m | 10.5 | C$_8$-C$_{10}$-glycoside | clear | clear | clear to −12° C., fluid |
| | | | | 10.5 | coconut alkyldimethylamine oxide | | | |
| | | | | | fatty alcohol | | | |
| 15 | 9 L | 70 | — | 10.5 | C$_8$-C$_{10}$-glycoside | clear | clear | clear to −12° C., fluid |
| | | | | 21 | coconut alkyldimethylbenzylammonium chloride fatty alcohol | | | |
| 16 | 6.5 L | 52.5 | — | 41 | C$_8$-C$_{10}$-glycoside fatty alcohol | clear | clear | clear to −20° C., fluid |
| 17 | 18 D,L | 61 | — | 10.5 | C$_8$-C$_{10}$-glycoside fatty alcohol | clear | clear | clear to at least −20° C., viscous but still flowable |
| | | | | 10.5 | coconut alkyldimethylaminoacetic acid (betaine) | | | |
| 18 | 18 D,L | 51 | 10 prop. m | 10.5 | fatty alcohol C$_8$-C$_{10}$-glycoside | clear | clear | clear to at least −20° C., fluid |
| | | | | 10.5 | coconut alkyldimethylaminoacetic acid (betaine) | | | |

(B) Biological Examples

Greenhouse-grown spring barley and spring wheat plants in the 3-leaf stage were sprayed with aqueous dilutions of the formulations with the active substance concentrations given in Table 2. The standard used was Comparison composition 1 given in Table 1. The plants were scored after 14-days. The damage (effect) is expressed as a percentage, and the results are listed in Table 2.

TABLE 2

Greenhouse experiment with spring barley and spring wheat
Percentage effect 14 days after treatment
Application rate, water: 300 l/ha

| Formulation from Table 1 No. | Dosage rate in g of active subst./ha | Spring barley | Spring wheat |
|---|---|---|---|
| Comparison composition 1 | 125 | 65 | 80 |
| | 250 | 83 | 85 |
| | 500 | 98 | 97 |
| | 1000 | 99 | 99 |
| 3 | 125 | 65 | 70 |
| | 250 | 85 | 83 |
| | 500 | 93 | 90 |
| | 1000 | 100 | 98 |
| 5 | 125 | 68 | 70 |
| | 250 | 85 | 90 |
| | 500 | 95 | 95 |
| | 1000 | 99 | 98 |
| 8 | 125 | 68 | 75 |
| | 250 | 85 | 85 |
| | 500 | 90 | 97 |
| | 1000 | 100 | 99 |
| 11 APG 225 ® Genaminox | 125 | 65 | 73 |
| | 250 | 80 | 83 |
| | 500 | 96 | 95 |
| | 1000 | 100 | 99 |
| 12 APG 225 ® Dodigen 226 | 125 | 60 | 65 |
| | 250 | 75 | 80 |
| | 500 | 90 | 90 |
| | 1000 | 95 | 93 |

We claim:

1. A liquid herbicidal composition comprising a compound of the formula I

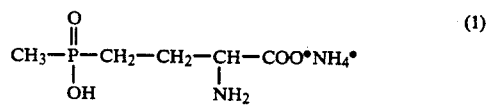

$$CH_3-\overset{\overset{O}{\|}}{\underset{OH}{P}}-CH_2-CH_2-\underset{NH_2}{CH}-COO^{\ominus}NH_4^{\oplus} \quad (1)$$

in the form of the stereoisomer mixture or of the L-enantiomer and a surfactant from the series of the (C$_8$-C$_{14}$)alkyl polyglycosides.

2. The composition as claimed in claim 1, additionally comprising at least one surfactant from the series
(C$_{10}$-C$_{18}$)-fatty alcohol polyglycol ether sulfate,
(C$_{12}$-C$_{18}$)alkyldimethylamine oxide,
(C$_{10}$-C$_{18}$)alkyldimethylbenzylammonium chloride and
coconut alkyldimethylaminoacetic acid (betaine), where, in the case of the ether sulfates, the alkali metal salts, ammonium salts or alkaline earth metal salts can be used.

3. The composition as claimed in claim 1, comprising 0.5 to 40 % by weight of active substance of the formula I.

4. The composition as claimed in claim 1, comprising 1 to 30 % by weight of active substance of the formula I.

5. The composition as claimed in claim 1, in which the amount of the surfactants, or surfactant mixture, defined in claim 1 or 2 is 0.5 to 8 % by weight per part of active substance.

6. The composition as claimed in claim 1, comprising 0 to 10 % of a water-miscible solvent.

7. The composition as claimed in claim 1, in which the amount of alkyl polyglycoside in the surfactant mixture as defined in claim 2 is not more than 50 % by weight.

8. The composition as claimed in claim 1, comprising further commercially available adjuvants, surfactants, wetting agents, dispersants, adhesion promoters, defoamers, preservatives and/or antifreeze agents.

9. The composition as claimed in claim 1, additionally comprising at least one further herbicidal active substance.

10. A method for using the surfactant as claimed in claim 1 or 2 as an additive to formulations comprising adding the surfactant to an active substance of formula I and, optionally, further herbicidal active substances.

11. A method for combating undesired vegetation, which comprises applying a preparation as claimed in claim 1 to plants, seeds of plants or to the area under cultivation.

* * * * *